United States Patent [19]
Finn et al.

[11] Patent Number: 5,512,034
[45] Date of Patent: Apr. 30, 1996

[54] SURGICAL INSTRUMENT INCLUDING VIEWING OPTICS AND A BALL PROBE

[76] Inventors: Miles A. Finn, 138 W. 49th St., Minneapolis, Minn. 55409; John C. Vanden Hoek, 11473 199th Ave., Elk River, Minn. 55330; Richard L. Shockey, 3003 121st La., NW., Coon Rapids, Minn. 55433; Thomas C. Barthel, 18251 62nd St., Becker, Minn. 55308

[21] Appl. No.: 233,013

[22] Filed: Apr. 25, 1994

Related U.S. Application Data

[63] Continuation-in-part of Ser. No. 981,641, Nov. 25, 1992, abandoned.

[51] Int. Cl.$^6$ ........................................................ A61B 8/00
[52] U.S. Cl. ............................ 600/138; 600/139; 606/13; 607/88
[58] Field of Search ................................... 128/4, 6, 7–23; 606/7, 13–17, 160, 161; 607/88, 89; 600/114, 121–123, 138–144

[56] References Cited

U.S. PATENT DOCUMENTS

| | | | |
|---|---|---|---|
| 4,802,461 | 2/1989 | Cho | 128/7 |
| 4,867,138 | 9/1989 | Kubota et al. | 128/6 |
| 5,156,604 | 10/1992 | Hessel et al. | 606/16 |
| 5,158,086 | 10/1992 | Brown et al. | 128/4 |
| 5,230,621 | 7/1993 | Jacoby | 128/6 |
| 5,337,735 | 8/1994 | Salerno | 128/11 |

*Primary Examiner*—Stephen C. Pellegrino
*Assistant Examiner*—Michael Peffley
*Attorney, Agent, or Firm*—Olson & Hierl, Ltd.

[57] ABSTRACT

A surgical instrument incorporating visualizing optics is disclosed. The instrument comprises a handle supporting a rigid, curved, hollow shaft, a spherical tip is located on the distal end of the shaft providing a surface that will not tear or easily penetrate tissue. A fiber-optic assembly, containing at least one illumination transmitting fiber, a plurality of image-carrying fibers and an objective lens mounted near the distal end of the image fibers runs the entire length of the shaft. The objective lens is mounted relative to an opening in the tip allowing either axial viewing or side viewing. Light for illuminating the surgical site passes through one or more illumination fibers and through the opening in the spherical tip of the probe. Light reflected from the tissue at the tip of the probe is focused onto the distal face of the image assembly by an objective lens and is then transmitted to the proximal end of the image assembly. Connectors on the proximal ends of the illumination fibers and image fibers facilitate their being coupled to an illumination source and a viewing device.

27 Claims, 1 Drawing Sheet

U.S. Patent  Apr. 30, 1996  5,512,034
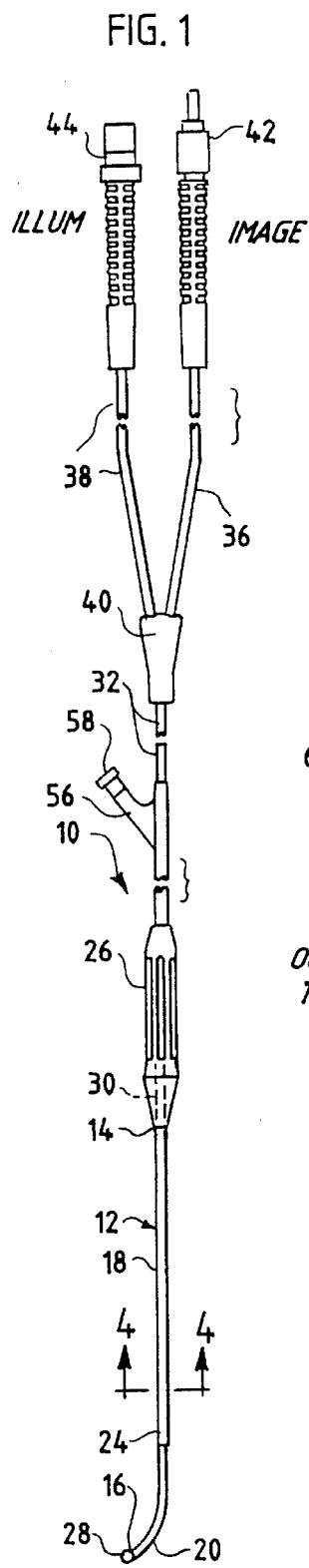
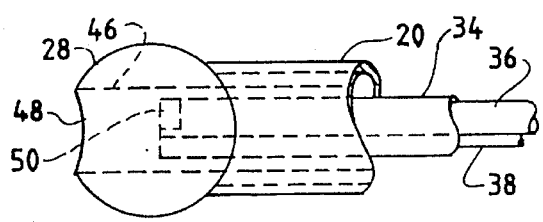
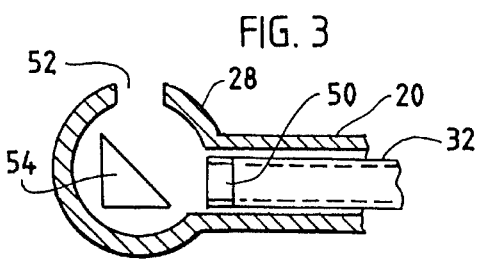
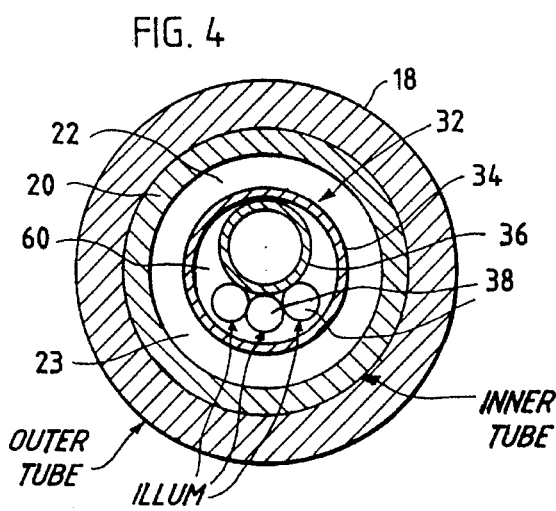
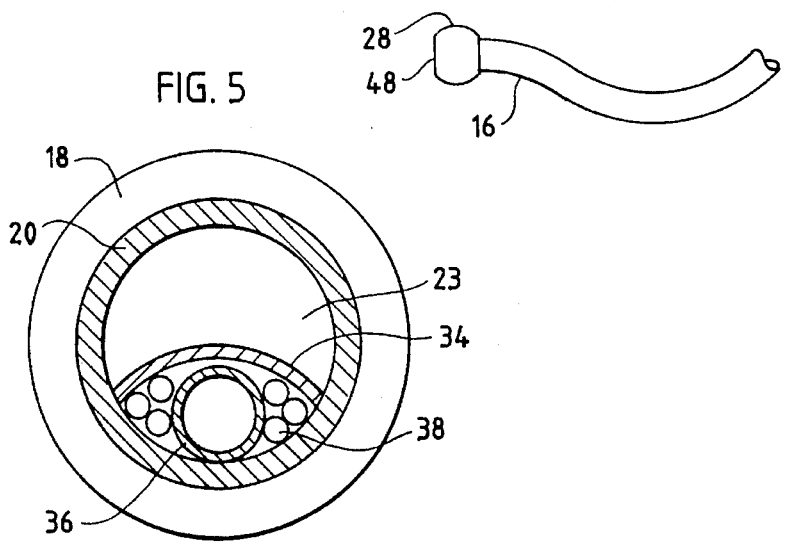

SURGICAL INSTRUMENT INCLUDING VIEWING OPTICS AND A BALL PROBE

RELATED APPLICATION

This application is a continuation-in-part of our earlier filed application Ser. No. 07/981,641 filed Nov. 25, 1992, abandoned.

FIELD OF THE INVENTION

This invention relates generally to surgical instruments, and more particularly to an instrument incorporating a probe for providing enhanced tactile response and use during surgery to touch and locate body structures hidden from direct view, the instrument also incorporating viewing optics whereby the structures being probed can also be indirectly viewed.

DISCUSSION OF THE PRIOR ART

During many surgical procedures, the surgeon is often required to reach into corners and around obstructions to feel tissue structures. For example, during a laminectomy/discectomy procedure, the surgeon is often required to determine whether a disc in the spine has become herniated to the point where it bulges out and compresses a nerve resulting in back pain. The surgeon opens up the back and excises part of the disc. Because the spinal canal protects the spinal cord, many important structures are hidden from direct access and view.

The surgeon then typically uses an L-shaped probe having an atraumatic tip, preferably bulbous, to reach under the dura mater to determine by sense of touch if the bulge in the disc has been sufficiently reduced by excision of the disc material so that pressure on the nerve will no longer occur. However, this can only be done by tactile feel because direct vision is not possible. Such a probe may also be used to allow tactile location of the foramen to determine if the spinal nerves are passing freely through the opening.

A probe of the type described is more clearly illustrated in *Microsurgery of the Spinal Cord and Surrounding Structures* by Wolfgang Seeger, Springer-Verlag, New York, 1982, pg. 363. Figure G on that page depicts a view through an operating microscope where a right-angled probe having a bulbous tip is reaching under the dura mater in the course of a laminectomy/discectomy procedure. While a skilled surgeon is able to deduce the state or condition of the disc structure by relying only on the tactile response provided by the L-shaped ball probe, the addition of a means for visualizing the tissue structures encountered by the probe tip would significantly enhance the safety and efficacy of the surgical procedure.

For such a probe to work, it must be small and light to provide the proper tactile feel. However, viewing around corners is not possible. Endoscope systems provide for viewing, but by their nature, are usually large and bulky. In addition, the distal end of a viewing system is generally ill suited to use for tactile sensing. Due to the bulky nature of such systems, the ends are not the right shape for direct contact and pressure on tissue and damage to tissue will usually result.

Other invasive probe systems are disclosed in Kubota et al. U.S. Pat. No. 4,867,138 entitled "Rigid Electronic Endoscope"; Hessel et al. U.S. Pat. No. 5,156,604 entitled "Small Probing Hook For Arthroscopy"; Brown et al. U.S. Pat. No. 5,158,086 entitled "Invasive Probe System"; Jacoby U.S. Pat. No. 5,230,621 entitled "Endoscopic Method And Device For Subgingival Dental Procedures"; and Heckele U.S. Pat. No. 4,593,682 entitled "Endoscope."

The probe disclosed in the Kubota et al. patent has an asymmetric tip with electronic imaging means. An opening is provided adjacent the tip and imaging means to provide a path for either an instrument or fluid to the exterior of the probe. Unfortunately, the device of the Kubota et al. patent does not possess effective tactile capabilities. Further, the image of the tissue provided by the Kubota et al. probe is obstructed by the instrument.

The probe disclosed in the Hessel et al. patent has a probing hook that has a slidable laser fiber guided at the distal end of the probing hook. The Hessel et al. patent discloses an arthroscopic instrument for diagnostic and therapeutic purposes, e.g. laser surgery, without an exchange of instruments. This device is not designed for endoscopic use. Because the probe of the Hessel et al. patent teaches the use of a displaceable laser fiber which extends beyond the probe, it is poorly suited for the combination of tactile feel and viewing.

The Brown et at patent discloses a probe system having a probe head that may provide imaging or combined imaging-treatment. The probe is resilient and articulated, which greatly limits its tactile capabilities. The addition of articulation results in a large shaft and bulky handle which makes good tactile feel by the surgeon difficult, if not impossible.

The Jacoby patent discloses a dental method and device for removing deposited material from subgingival tooth surfaces. An optical head is positioned adjacent a working part or blade of the instrument and aimed at an angle to permit illumination and endoscopic visualization of an area immediately in front of the leading edge of the working part or blade of the instrument. Because the view of the working area is obstructed by the working part, the device has limited endoscopic capabilities. The device also has limited tactile capabilities because the hook-shaped construction prevents effective response in all directions. In fact, the Jacoby device is not designed for tactile feel but to scrape deposits off teeth.

The probe disclosed in the Heckele patent has a rigid distal longitudinal member having a distal extremity which may be angled. A light duct and an image duct having an objective lens are also included. The Heckele patent probe is used simply to view the prefrontal sinuses and does not possess effective tactile capabilities.

What is needed is a small, easy to use instrument which provides good tactile feel of the tissues so the surgeon can use his sense of touch to make judgments about the tissue. The instrument should also provide for viewing by the surgeon so that a combination of sight and feel can be used. The present invention meets these desires.

SUMMARY OF THE INVENTION

The present invention provides an improved surgical instrument for use in the conduct of surgical procedures. The surgical instrument has a bulbous atraumatic tip and includes endoscopic viewing capabilities so that the surgeon can both feel and see tissue structures which would otherwise be hidden from direct view. The combination of viewing optics and a ball probe allows tissue structures not otherwise visible through an incision to be felt and observed at the same time.

The surgical instrument includes an elongated, rigid shaft having a proximal end, a distal end and a lumen extending between the ends. A handle is affixed to the proximal end of the shaft and an atraumatic, generally bulbous rigid tip, preferably in the form of a generally oblate sphere or ball, is formed on or otherwise attached to the distal end of the tubular shaft for enhanced tactile response. The tip defines an opening leading to a chamber which is in communication with the lumen of the shaft. The opening may be coaxial with the lumen.

A fiber-optic assembly, including a plurality of optical image fibers as in a bundle and, preferably, one or more illumination fibers, extends through the lumen of the shaft. The distal end of the optical image fibers have a planar face. An objective lens, cooperating with the distal end of the image fibers, is mounted within the chamber of the bulbous tip to receive light rays entering the opening formed in the tip and create an image on the face of the image fibers.

The fiber-optic assembly also passes through a bore in the handle, and preferably on its proximal end are first and second connectors for coupling the illumination fibers in the fiber-optic assembly to an external light source and the image fibers to an appropriate display device, such as an eyepiece or a video camera and an associate CRT display terminal.

The surgical instrument of the present invention can also be used with another surgical instrument during a surgical procedure. For instance, the surgical instrument of the present invention may be inserted into the body for palpating and viewing tissue. Because the tip of the present invention displaces tissue (relative to its diameter) a space may be created between the tissue such that another instrument, such as another surgical instrument according to the present invention, may also be inserted into the body and positioned relative to the other surgical instrument to view this space. The second instrument thus provides a viewing perspective of the image provided by the first instrument.

BRIEF DESCRIPTION OF THE DRAWINGS

The foregoing features and advantages of the invention will become more apparent to those skilled in the art from the following detailed description of the preferred embodiment, especially when considered in conjunction with the accompanying drawings in which:

FIG. 1 is a side elevation view of the surgical instrument constructed in accordance with the present invention;

FIG. 2 is a greatly enlarged view of the atraumatic tip on the surgical instrument of FIG. 1;

FIG. 3 is a greatly enlarged cross-sectional view of the atraumatic tip portion of the surgical instrument of FIG. 1 when constructed in accordance with an alternative embodiment;

FIG. 4 is a cross-sectional view taken along the plane 4—4 in FIG. 1;

FIG. 5 is an alternative cross-sectional design similar to that of FIG. 4; and

FIG. 6 is an alternative embodiment for the distal end of the instrument.

DESCRIPTION OF THE PREFERRED EMBODIMENT

Referring to FIG. 1, there is illustrated a surgical instrument constructed in accordance with the present invention identified generally by numeral 10. The instrument 10 comprises an elongated rigid tubular shaft 12 having a proximal end 14 and a distal end 16. As can be seen from the greatly enlarged cross-sectional view of FIG. 4, the shaft 12 preferably includes an outer tube 18 surrounding an inner tube 20 with the inner tube 20 defining a lumen 22 extending between the proximal end 14 and the distal end 16. The outer tube 18 terminates at 24 (FIG. 1), which is a predetermined distance proximal of the distal end 16 of the instrument 10.

Outer tube 18 and inner tube 20 provide greater rigidity to the instrument in the zone proximal of the terminus 24 of the outer tube 18. The outer tube 18 may be formed from stainless steel. The rigidity provided by the coaxially disposed tubular shaft 12 further enhances the tactile response of the instrument 10. The inner tube 20 may be constructed of stainless steel or, if desired a material that is somewhat more malleable such that it is capable of being bent by the surgeon and still maintain the instrument's tactile response for use as a tactile probe.

Referring again to FIG. 1, it can be seen that the proximal end 14 of the shaft 12 is joined to a handle 26. It is preferred that shaft 12 is generally tapered from the proximal end 14 to the distal end 16, which provides greater rigidity and further enhances tactile response of the shaft at its proximal end 14. In accordance with the preferred embodiment, a segment of the inner tube 20, which is proximal of the terminus 24 of the outer tube 18, is arcuate with a bend having a desired angle in the range of from about 20 degrees up to 90 degrees, and a length in the range of from about 8 mm to 15 mm. Integrally formed on or otherwise affixed to the distal end 16 of the shaft 12 is a rigid, atraumatic bulbous tip 28. The tip 28 is preferably generally spherical in shape and of a size which would not tend to penetrate into the tissue being probed. The sphere or ball tip 28 may have a diameter of about 3 mm., but that size is only indicated for the purpose of illustration.

The desired diameter of the tip 28 varies according to its intended use. The tip 28 may have a different diameter depending on its use. For example, the diameter of tip 28 may be smaller than 3 mm for use in the cervical spine. It is preferable that the diameter of tip 28 be greater than the diameter of the distal end 16 to enhance tactile feedback.

The present invention also contemplates other shapes for tip 28, such as the prolate or oblate tip shown in FIG. 6. Typically, prolate tips pass through tissue easily whereas oblate tips provide better tactile response. The tip is preferably rigid or incompressible in order to facilitate tactile response.

A bore 30 is formed longitudinally through the handle 26 and that bore is preferably in generally coaxial alignment with the lumen 22 of the inner tube 20. Passing through the bore 30 and the lumen 22 is a fiber-optic assembly 32.

In accordance with the embodiment of FIG. 4, the fiber-optic assembly 32 preferably includes an outer sheath 34 surrounding an assembly of image fibers 36 and preferably at least one, or more preferably several, illumination fibers 38. Preferably, an annular space 23 is formed in the lumen 22 between inner tube 20 and sheath 34 as illustrated in FIG. 4. This space can be used to introduce a flushing fluid as discussed below.

In the alternative embodiment of FIG. 5, however, the image fibers 36 and illumination fibers 38 are not axially disposed. Instead, image fibers 36 and illumination fibers 38 are located between inner tube 20 and sheath 34. This configuration defines a space 23 having less surface area and a greater cross-section area than space 23 in FIG. 4 to provide greater conduction of fluid with less pressure.

Typically, an irrigation fluid flow rate of about 25 cc/min. is required to clear blood away from lens 50 during a surgical procedure. However, most pressure cuffs provide up to about 300 mm Hg pressure. Some lumen configurations may not be able to achieve that flow rate with this pressure. Space 23 of FIG. 5, however, can provide that rate with this pressure.

Referring back to FIG. 1, disposed proximal of the handle 26 is a molded plastic hub member 40 surrounding a junction where the illumination fibers 38 and the image fibers 36 bifurcate into separate branches. Affixed to the proximal end of the assembly of image fibers 36 is a connector 42 which is adapted to mate with a viewing device (not shown), such as an optical eyepiece or a video camera providing a desired degree of magnification. The illumination fibers 38 also terminate at their proximal end in a connector 44 which is adapted to connect to a light source (not shown).

In the embodiments of FIGS. 2 and 6, the atraumatic (ball) tip 28 defines an opening 48 leading to a hollow chamber 46 formed within the tip. Preferably, the chamber has a diameter large enough to receive distal end 16 of the shaft. The chamber 46 communicates with the generally circular surface opening 48 through the sphere's surface at its most distal end. Fiber-optic assembly 32 terminates within the hollow chamber 46 and an objective lens 50 is provided at the distal end of the image fibers 36 in assembly 32. By mounting the objective lens 50 a predetermined distance relative to the surface opening 48 in the distal end of the bulbous tip, the distal surface of the tip used for probing tissue can be brought into the focus range of the lens. Further, the tool itself does not obstruct the view of the tissue being probed and the lens 50 does not contact the tissue while in use. This allows for probing and viewing simultaneously without changing the configuration of the instrument.

As can be seen in FIG. 1, the arcuate bend in inner tube 20 may be less than 90 degrees. As the arcuate bend in the tube 20 approaches 90 degrees, however, stress between the interface of the lens 50 and image fibers 36 is increased. To overcome this, it is preferred in the present invention to increase the distance between the arcuate bend in tube 20 and tip 28. To further lessen this stress, another bend can be located proximal to distal end 16 as illustrated in FIG. 6.

When a source of light is coupled to the connector 44, it passes through the illumination fibers 38 and out through the opening 48 in the spherical tip 28. Objects illuminated by such light reflect an image back through the objective lens 50 and the image fibers within the image assembly 36 to the viewing device (not shown) coupled to the connector 42.

In use, the surgeon is able to insert the instrument through a surgically created opening in the body and then by manipulating the handle can position the instrument so as to feel tissue structures of interest. Because of the incorporation of the fiber-optic assembly 32 within the instrument, the tissue structures being approached and felt with the atraumatic tip 28 can also be visually observed.

While FIG. 2 depicts an end-viewing instrument, the cross-sectional view of FIG. 3 shows the manner in which the atraumatic tip can be modified to offer a side-viewing instrument. The bulbous or spherical tip 28 in FIG. 3 is generally hollow and has an opening 52 formed therein which is at an angle, approximately 90 degrees as illustrated, to the longitudinal axis of the shaft 20. Suitably disposed within the confines of the hollow spherical tip 28 is an optical means, such as a prism or mirror 54, which is positioned to refract or reflect light emanating from the ends of the illumination fibers 38 within the assembly 32 out through the opening 52. Prism 54 picks up the reflected image observed through the opening 52 and presents it on the objective lens 50. The prism preferably has a plurality of facets and a reflective surface on at least one of the facets.

Referring once more to FIG. 1, a Y-fitting 56 having a Luer lock 58 on its proximal end is joined to the handle 26 and contains a lumen that is in fluid communication with the lumen 22 in the shaft 12. This allows a source of irrigation or flushing liquid to be injected through the Luer fitting 58 and the Y-fitting 56 so that it will exit the lumen 22 of the fiber-optic assembly 32 in a fashion to insure that the objective lens 50 can be flushed clean of blood or other debris that might otherwise occlude the image being viewed.

Using the annular space defined between tubes 18 and 20, and the outer sheath 34 minimizes the diameter of the shaft 12 and maximizes the possible flow rate of flushing liquid. This provides an annular flush that spreads fluid around the circumference of fiber-optic assembly 32 of the distal end 16 and out the space 23 to insure clearness in the entire field of view of fiber-optic assembly 32. This same annular space or channel or, alternatively, a separate lumen or channel can be used to aspirate fluids. As a further alternative, a separate channel or lumen as shown in FIG. 5 disposed parallel to fiber-optics assembly 32 can also be used for providing the flushing liquid. These separate lumen or channels are preferably located within shaft 12.

For example, the outside diameter of the shaft member or outer tube 18 may be approximately ⅛ in. and may be about 5 in. long. The shaft portion or inner tube 20 may be about 1 in. in length and 2 mm. in diameter.

The number of illumination fibers and their diameters are selected to provide adequate light intensity. Typically, there might be three plastic illumination fibers, each of a diameter of 250 microns. Alternatively, approximately 100 glass fibers of 50 micron diameter each might be used. The light emitted by the illumination fibers illuminates the tissue exterior to the tip 28 to be viewed. Light reflected from the tissue is collected by the objective lens 50 and focused on a preferred planar face defined by the distal ends of image fibers 36 of fiber-optic assembly 32. Typically, this assembly including image fibers 36 may include up to 10,000 individual glass fibers which provides excellent resolution of the image focused by the objective lens 50.

While the embodiment illustrated in the drawings shows only a single fiber-optic assembly traversing the length of the probe and cooperating with an opening formed in the bulbous atraumatic tip thereof, it is also contemplated that a second fiber-optic assembly may also be routed through the handle and shaft of the instrument and have its objective lens properly positioned relative to the opening to provide a binocular view along separate optical axes.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A tactile surgical instrument for palpating and viewing tissue comprising:

(a) an elongated rigid shaft having a proximal end, a distal end and a lumen extending between the ends;

(b) a handle connected to the proximal end of the shaft, the handle including a longitudinal bore communicating with the lumen;

(c) a rigid bulbous atraumatic tip joined to the distal end of the shaft for providing enhanced tactile response, the tip defining a surface opening leading to a chamber in the tip that communicates with the lumen; and (d) a fiber-optic viewing assembly including a plurality of optical image fibers having a planar face at the distal end thereof, the assembly including an objective lens mounted within the chamber for creating an optical image of tissue proximal to the opening onto the face of the image fibers, the assembly being mounted to extend through the lumen and terminating within the chamber such that the tissue can be palpated and viewed simultaneously.

2. The surgical instrument of claim 1 wherein the lumen and fiber-optic assembly define a space between them which is in fluid communication with the opening to allow a flushing fluid to be sent through the lumen and out the opening.

3. The surgical instrument of claim 2 wherein the fluid enters the chamber about the objective lens.

4. The surgical instrument of claim 1 wherein the tip is generally spherical and symmetrically joined on the shaft and has a diameter about twice that of the shaft to permit tissue to close about the shaft and open in front of the opening.

5. The surgical instrument of claim 1 wherein the objective lens is recessed a predetermined distance from the opening such that tissue at the opening is in focus.

6. The surgical instrument of claim 5 including flushing means for introducing a flushing fluid into the chamber about the lens.

7. The surgical instrument of claim 1 wherein the shaft includes an arcuate bend proximal of the atraumatic tip.

8. The surgical instrument of claim 1 wherein the axis of the fiber-optic assembly is eccentric to the axis of the lumen.

9. The surgical instrument of claim 1 wherein the atraumatic tip is generally spherical and has a diameter greater than that of the shaft at the distal end thereof.

10. The surgical instrument of claim 1 further including at least one illumination fiber extending through the longitudinal bore and the lumen for transmitting light energy from an external source proximal of the handle and through the opening.

11. The surgical instrument of claim 10 wherein the at least one illumination fiber and the plurality of image fibers are contained within a common sheath.

12. The surgical instrument of claim 10 further including means for injecting an irrigating fluid into the chamber.

13. The surgical instrument of claim 1 wherein the opening in the tip is generally coaxial with the lumen.

14. The surgical instrument of claim 1 wherein the opening is located at an angle to a longitudinal axis of the lumen.

15. The surgical instrument of claim 14, further including optical means mounted within the chamber of the tip for directing light rays entering the opening onto the objective lens.

16. The surgical instrument of claim 15 wherein the optical means includes a prism having a plurality of facets and a reflective surface on at least one of the facets.

17. The surgical instrument of claim 1 wherein the objective lens is recessed within the chamber a predetermined distance from the opening.

18. The surgical instrument of claim 1 wherein at least a portion of the shaft is malleable by a user.

19. A surgical instrument comprising:

(a) an elongated rigid shaft having a proximal end, a distal end and a lumen extending between the ends, the shaft including inner and outer tubes, the inner tube extending beyond the outer tube and being malleable by a user;

(b) a handle affixed to the proximal end of the shaft, the handle including a longitudinal bore communicating with the lumen;

(c) a generally rigid spherical tip joined symmetrically to the distal end of the shaft and having a greater diameter than the diameter of the shaft for providing enhanced tactile response, the tip defining an opening leading to a chamber in the tip, and communicating with the lumen; and (d) a fiber-optic assembly mounted in the chamber and the lumen for creating, at a remote location, a viewable image of tissue located proximal and exterior to the tip.

20. The surgical instrument of claim 19 wherein the fiber-optic assembly has a proximal end and a distal end and including at least one illumination fiber, a plurality of image fibers and an objective lens affixed to the distal end, the objective lens mounted in the tip to receive light traversing the illumination fiber and reflected from an object being viewed.

21. The surgical instrument of claim 20 further including flushing means for injecting a flushing liquid through the lumen for maintaining the objective lens clean of blood and debris.

22. The surgical instrument of claim 19 wherein the shaft is generally tapered from the proximal end to the distal end.

23. The surgical instrument of claim 19 wherein an annular space is defined between the shaft, the tip and the fiber-optic assembly within the lumen and bore to provide flushing liquid to the tip.

24. The surgical instrument of claim 19 wherein the shaft includes a flush lumen therein parallel to the fiber-optic assembly to provide liquid to the opening.

25. The surgical instrument of claim 19 wherein the outer tube is less malleable than the inner tube.

26. A tactile surgical instrument for palpating and viewing tissue comprising:

(a) an elongated rigid shaft having a proximal end, a distal end and a lumen extending between the ends;

(b) a handle connected to the proximal end of the shaft, the handle including a longitudinal bore communicating with the lumen;

(c) a rigid bulbous atraumatic tip joined to the distal end of the shaft for providing enhanced tactile response, the tip defining a surface opening leading to a chamber in the tip that communicates with the lumen; and (d) a fiber-optic viewing assembly including a plurality of optical image fibers having a planar face at the distal end thereof, the assembly extending through the shaft and including an objective lens mounted within the chamber for creating an optical image of tissue proximal to the surface opening onto the face of the image fibers, the assembly terminating within the chamber such that the tissue can be palpated and viewed simultaneously, the lumen being in fluid communication with the surface opening to allow a fluid to be sent through the lumen, about the objective lens and out the opening.

27. The surgical instrument of claim 26 wherein the fiber-optic viewing assembly is disposed in the lumen.

* * * * *